(12) United States Patent
Park et al.

(10) Patent No.: US 7,736,880 B2
(45) Date of Patent: Jun. 15, 2010

(54) MICROORGANISM OF CORYNEBACTERIUM GENUS HAVING RESISTANCE TO KANAMYCIN AND ENHANCED L-LYSINE PRODUCTIVITY AND METHOD OF PRODUCING L-LYSINE USING THE SAME

(75) Inventors: Young Hoon Park, Seongnam (KR); Sang Jo Lim, Incheon (KR); Jun Ok Moon, Seoul (KR); Jin Suck Sung, Yongin (KR)

(73) Assignee: CJ Cheiljedang Corporation (KR)

( * ) Notice: Subject to any disclaimer, the term of this patent is extended or adjusted under 35 U.S.C. 154(b) by 557 days.

(21) Appl. No.: 11/562,099

(22) Filed: Nov. 21, 2006

(65) Prior Publication Data

US 2007/0122889 A1    May 31, 2007

(30) Foreign Application Priority Data

Nov. 30, 2005 (KR) .................. 10-2005-0115905

(51) Int. Cl.
*C12N 1/20* (2006.01)
*C12P 13/08* (2006.01)

(52) U.S. Cl. .................. 435/252.1; 435/115; 435/843

(58) Field of Classification Search .............. 435/252.1, 435/254.2, 115, 843, 252.32, 69.8
See application file for complete search history.

(56) References Cited

U.S. PATENT DOCUMENTS

| | | | |
|---|---|---|---|
| 4,623,623 A | 11/1986 | Nakanishi et al. | |
| 5,268,293 A | 12/1993 | Oh et al. | |
| 2005/0196848 A1 | 9/2005 | Dusch et al. | |
| 2007/0122889 A1 | 5/2007 | Park et al. | |

FOREIGN PATENT DOCUMENTS

| | | | |
|---|---|---|---|
| CN | 1304997 A | | 7/2001 |
| EP | 1 096 013 A2 | * | 5/2001 |
| FR | 2 645 172 A1 | * | 10/1900 |
| WO | 02/053707 A1 | | 7/2002 |

OTHER PUBLICATIONS

Schrumpf et al., Isolation and prominent characteristics of an L-lysine hyperproducing strain of Corynebacterium glutamicum, Applied Microbiology and Biotechnology, 1992, pp. 566-571, vol. 37, XP-000979296.
European office action for 06 256 098.2-2401. 4 pages.
Chinese office action for 200610163706.5 with partial English translation. 7 pgs.
Ikeda, et al., "The Corynebacterium glutamicum genome: features and impacts on biotechnological processes", Appl. Microbiol Biotechnol, 2003, vol. 62, pp. 99-109.
Ohnishi, et al., "A Novel gnd Mutation Leading to Increased L-lysine Production in Corynebacterium Glutamicunn", FEMS Microbiology Letters, 2005, vol. 242, pp. 265-274.

* cited by examiner

*Primary Examiner*—Maria Leavitt
(74) *Attorney, Agent, or Firm*—Rothwell, Figg, Ernst & Manbeck, PC

(57) ABSTRACT

Provided are a microorganism of *Corynebacterium* genus capable of producing L-lysine and resistant to kanamycin, and a method of producing L-lysine using the same.

1 Claim, No Drawings

MICROORGANISM OF CORYNEBACTERIUM GENUS HAVING RESISTANCE TO KANAMYCIN AND ENHANCED L-LYSINE PRODUCTIVITY AND METHOD OF PRODUCING L-LYSINE USING THE SAME

CROSS-REFERENCE TO RELATED PATENT APPLICATION

This application claims the benefit of Korean Patent Application No. 10-2005-0115905, filed on Nov. 30, 2005, in the Korean Intellectual Property Office, the disclosure of which is incorporated herein in its entirety by reference.

BACKGROUND OF THE INVENTION

1. Field of the Invention

The present invention relates to a microorganism of *Corynebacterium* genus having resistance to kanamycin and capable of producing L-lysine and a method of producing L-lysine using the same.

2. Description of the Related Art

Coryneform bacteria are microorganisms that belong to the genus *Corynebacterium* and *Brevibacterium*.

L-lysine is an essential amino acid widely used for animal feed, medical supplies and foods. In particular, the amount of L-lysine used in 2004 was reported to be about 0.8 million tons and demand for L-lysine is expected to continuously increase by an average of about 10% yearly in the future.

L-lysine is produced by direct fermentation using a microorganism such as *E. Coli*, *Corynebacteria* or the like, and thus development of producing microorganisms having enhanced yield or L-lysine productivity enhanced by improvement of a fermentation process have a large economical effect.

L-lysine is produced by known methods using bacteria such as various kinds of auxotrophic mutant, various kinds of bacteria resistant to drugs, various kinds of bacteria sensitive to drugs and various kinds of bacteria resistant to antibiotics. Of these methods, it is known that a method using bacteria resistant to antibiotics includes a method using various bacteria resistant to several antibiotics such as rifampicin and streptomycin, etc. (see, for example U.S. Pat. No. 4,623,623).

However, bacteria that have resistance to kanamycin, a kind of aminoglycoside-based antibiotic, and produce L-lysine have not been reported.

The inventors of the present invention conducted extensive research about a method of producing L-lysine using a microorganism of *Corynebacterium* genus by direct fermentation to reduce production costs of L-lysine and increase yield of L-lysine, and found that L-lysine productivity can be enhanced by giving the microorganism of *Corynebacterium* genus resistance to kanamycin, thus completing the present invention.

SUMMARY OF THE INVENTION

The present invention provides a microorganism of *Corynebacterium* genus having resistance to kanamycin and capable of producing L-lysine. The present invention also provides a method of producing L-lysine with a high yield using the microorganism.

DETAILED DESCRIPTION OF THE INVENTION

According to an aspect of the present invention, there is provided a microorganism of *Corynebacterium* genus capable of producing L-lysine and resistant to kanamycin.

The microorganism can be any microorganism of *Corynebacterium* genus capable of producing L-lysine, and resistant to kanamycin. For example, the microorganism of *Corynebacterium* genus may be *Corynebacterium glutamicum* ATCC 13032, *Corynebacterium thermoaminogenes* FERM BP-1539, *Corynebacterium glutamicum* KFCC 10881, and *Corynebacterium glutamicum* KFCC 11001, which are resistant to kanamycin, but is not limited thereto.

A microorganism of *Corynebacterium* genus according to an embodiment of the present invention is a variant of *Corynebacterium glutamicum* KFCC10881 which is resistant to S-(2-amino ethyl)cysteine, α-amino-β-hydroxyl valeric acid, methyl lysine and sodium azide, and has a requirement for leucine and a leaky requirement for homoserine, and the variant is resistant to kanamycin. In the current embodiment of the present invention, the variant is *Corynebacterium glutamicum* KFCC10881-CJP5103 (Accession No. KCCM-10707P).

The microorganism of *Corynebacterium* genus can be obtained by inducing mutation in a microorganism of *Corynebacterium* genus capable of producing L-lysine using a known method of mutagenesis, and then culturing the resulting product in the presence of kanamycin. The mutation can be induced by exposing the microorganism of *Corynebacterium* genus capable of producing L-lysine to a mutagenic agent, for example, radioactive radiation or mutagenic compounds. In addition, site directed mutagenesis can be used, but mutagenesis is not limited to those methods.

*Corynebacterium glutamicum* KFCC10881-CJP5103 (Accession No. KCCM-10707P) according to an embodiment of the present invention can be produced by giving a kanamycin resistance to a parent strain, *Corynebacterium glutamicum* KFCC10881, using a chemical mutagenic agent, N-methyl-N'-nitro-N-nitrosoguanidine.

In particular, $10^7$-$10^8$/ml of the parent strain are treated with N-methyl-N'-nitro-N-nitrosoguanidine which is a mutagen at 30° C. for 30 minutes to reach a final concentration of 500 µg/ml, and bacteria growing in a minimal agar plate medium containing kanamycin having a concentration of 5 mg/l are separated to obtain the mutant having resistance to kanamycin. In addition, the mutant according to the current embodiment of the present invention can be obtained by culturing the mutant having resistance to kanamycin, comparing L-lysine productivity of bacteria with one another, and selecting bacteria having improved L-lysine productivity.

The parent strain, *Corynebacterium glutamicum* KFCC10881, and the mutant having resistance to kanamycin obtained therefrom have characteristics described as follows.

Parent strain, *Corynebacterium glutamicum* KFCC10881: has resistance to S-(2-amino ethyl)cysteine, resistance to α-amino-β-hydroxyl valeric acid, resistance to methyl lysine, and resistance to sodium azide, and has a leaky requirement for homoserine and has a requirement for leucine.

Mutant, *Corynebacterium glutamicum* KFCC10881-CJP5103: has resistance to S-(2-amino ethyl)cysteine, resistance to α-amino-β-hydroxyl valeric acid, resistance to methyl lysine, and resistance to sodium azide, and has a leaky requirement for homoserine, and has a requirement for leucine and resistance to kanamycin.

In the current embodiment of the present invention, kanamycin is a kind of aminoglycoside-based antibiotic, and interferes with protein synthesis by binding with ribosome participating in protein biosynthesis, thereby having the antibiotic ability.

As described above, the microorganism of the present invention has resistance to kanamycin, and improved L-lysine productivity. In the process of giving resistance to kanamycin to the parent strain, it is considered that a gene participating in menaquinone biosynthesis is inactivated, and as a result, a mutant strain of which electron transporting activity is reduced is obtained. Due to the reduced electron transport activity, it is deemed that an oxygen requirement of the bacteria is also reduced, and production yield of L-amino acid increases, accordingly. However, a mechanism of the microorganism according to the current embodiment of the present invention is not limited to these specific mechanisms.

The present invention also provides a method of producing L-lysine including culturing the microorganism according to an embodiment of the present invention; and collecting L-lysine from the culture.

In the method according to the current embodiment of the present invention, the microorganism of the genus *Corynebacterium* may be cultured using any culture conditions and method known in the art. An example of a culture medium for culturing the *Corynebacterium* strain is the culture medium disclosed in the Manual of Methods for General Bacteriology by the American Society for Bacteriology (Washington D.C., USA, 1981). Carbohydrate sources that can be used in the medium include the following: sugars and carbohydrates such as glucose, saccharose, lactose, fructose, maltose, starch and cellulose; oils and fats such as soybean oil, sunflower oil, castor oil, and coconut oil; fatty acids such as palmitic acid, stearic acid and linolenic acid; alcohols such as glycerol, ethanol; and organic acids such as acetic acid. The examples of sugar sources mentioned above can be used alone or in combination. Examples of nitrogen sources include the following: peptone, yeast extracts, meat extracts, malt extracts, corn steep liquor, soybean meal, and urea or inorganic compounds such as ammonium sulfate, ammonium chloride, ammonium phosphate, ammonium carbonate, and ammonium nitrate. Examples of phosphorus sources include the following: potassium dihydrogen phosphate, dipotassium hydrogen phosphate, or corresponding sodium salts thereof. Also, the culture medium can include metal salts, such as magnesium sulfate or iron sulfate, which is necessary for growth. In addition, essential materials for growth such as amino acids and vitamins can be used in addition to the above ingredients. Moreover, proper precursors can be used in the culture medium. The above ingredients can be added to the culture medium during the cultivation in a batchwise or continuous manner.

The pH of the culture medium can be controlled using a basic compound such as sodium hydroxide, potassium hydroxide or ammonia, or an acid compound such as phosphoric acid or sulphuric acid. Also, the use of an antifoaming agent such as fatty acid polyglycol ester can suppress foam generation. Oxygen or an oxygen-containing gas such as air can be injected into the medium in order to maintain aerobic condition. The temperature of the culture medium may be 20 to 45° C., preferably 25 to 40° C. The culturing can be performed until a desired quantity of L-lysine is produced, but the culturing is desirably performed for 10 to 160 hours.

The culturing can be performed in a continuous manner using a batch, fed batch, repeated fed batch or batchwise method. These methods are well known in the art, and the present invention is not limited thereto.

L-amino acid can be collected from a culture by treating a culture medium with a sulphuric acid or a hydrochloric acid and then using in combination with methods such as anion exchange chromatography, concentration, salting out, isoelectric point precipitation, etc.

The present invention will now be described in further detail with reference to the following examples. These examples are for illustrative purposes only, and are not intended to limit the scope of the present invention.

EXAMPLES

Example 1

Production of a Mutant of *Corynebacterium Glutamicum* KFCC10881 Having Resistance to Kanamycin A mutant of *Corynebacterium glutamicum* KFCC10881 having resistance to kanamycin and improved L-lysine productivity was selected from the product obtained by mutagenizing *Corynebacterium glutamicum* KFCC10881 as a parent bacteria with a chemical mutagen, N-methyl-N'-nitro-N-nitrosoguanidine.

First, $10^7$-$10^8$/ml of the parent bacteria are treated with N-methyl-N'-nitro-N-nitrosoguanidine, at 30° C. for 30 minutes to reach a final concentration of 500 µg/ml. Next, the mutagenized microorganism was cultured in a minimal agar plate medium containing kanamycin having a concentration of 5 mg/l to separate growing bacteria. In addition, the separated mutants were cultured, and L-lysine productivity thereof was measured to select bacteria having a maximum production ability of L-lysine from the separated mutants.

The obtained mutant having resistance to kanamycin was named *Corynebacterium glutamicum* KFCC10881-CJP5103, deposited on Nov. 16, 2005 at the Korean Culture Center of Microorganisms (KCCM), 361-221, Yurim B/D, Hongje-1-dong, Seodaemun-gu, Seoul 120-091, Repub. of Korea, and had Accession No. KCCM-10707P.

The mutant obtained in Example 1 and the parent bacteria have characteristics as follows.

Parent bacteria, *Corynebacterium glutamicum* KFCC10881: resistance to S-(2-amino ethyl)cysteine, resistance to α-amino-β-hydroxyl valeric acid, resistance to methyl lysine, resistance to sodium azide, and a leaky requirement for homoserine, and a requirement for leucine.

Mutant, *Corynebacterium glutamicum* KFCC10881-CJP5103: resistance to S-(2-amino ethyl)cysteine, resistance to α-amino-β-hydroxyl valeric acid, resistance to methyl lysine, resistance to sodium azide, and a leaky requirement for homoserine and a requirement for leucine and resistance to kanamycin.

Next, an experiment of resistance to kanamycin with respect to the selected mutant resistant to kanamycin, *Corynebacterium glutamicum* KFCC10881-CJP5103, and the parent bacteria was performed. First, the two microorganisms were cultured in a Luria Bertani (LB) liquid medium for 16 hours, and then the cells were washed using sterile normal saline two times. Then, the washed cells were properly diluted and the resulting product was cultured in a minimal agar plate medium containing kanamycin having a concentration of 5 mg/l for four days to measure productivity of each microorganism. A composition of the minimal agar plate medium is the same as follows: 10 g of glucose, 2 g of $(NH_4)_2SO_4$, 2 g of urea, 1.0 g of $KH_2PO_4$, 3.0 g of $K_2HPO_4$, 0.5 g of $MgSO_4.7H_2O$, 10 mg of $FeSO_4.7H_2O$, 10 mg of $MnSO_4.7H_2O$, 100 µg of biotin, 100 µg of thiamine.HCl, 100 µg of $CaCl_2.2H_2O$, 80 µg of $Na_2B_4O_7.10H_2O$, 40 µg of $(NH_4)_6MoO_{27}.4H_2O$, 10 µg of $ZnSO_4.7 H_2O$, 300 µg of $CuSO_4.7 H_2O$, 10 µg of $MnCl_2.4H_2O$, 1 mg of $FeCl_3.6H_2O$, 20 g of agar, 0.1 g of L-leucine if necessary, 0.1 g of L-threonine if necessary, 0.1 g of L-methionine if necessary, per 1 L of distilled water (pH 7.0).

The results of measuring productivity of the mutant and the parent bacteria in a kanamycin-containing medium are shown in Table. 1.

TABLE 1

Resistance to kanamycin of *Corynebacterium glutamicum* KFCC10881 and *Corynebacterium glutamicum* KFCC10881-CJP5103

| Kanamycin (mg/l) | KFCC-10881 | KFCC-10881-CJP5103 |
|---|---|---|
| | +++ | +++ |
| | − | +++ |

+++: sufficient growth
−: no growth

Example 2

Confirmation of L-lysine Productivity of *Corynebacterium Glutamicum* KFCC10881-CJP5103

*Corynebacterium glutamicum* KFCC10881 and *Corynebacterium glutamicum* KFCC10881-CJP5103 were inoculated in a 250 ml corner-baffled flask containing 25 ml of the seed medium below, and the resulting product was cultured at 30° C. for 20 hours while being stirred at 220 rpm. Next, 1 ml of the obtained culture medium was inoculated in a 250 ml corner-baffled flask containing 25 ml of the production medium below, and the resulting product was cultured at 32° C. for 96 hours while being stirred at 220 rpm.

After cultivation was terminated, L-lysine production was measured by high pressure liquid chromatography (HPLC). Amounts of L-lysine in the culture of *Corynebacterium glutamicum* KFCC10881 and *Corynebacterium glutamicum* KFCC10881-CJP5103 were represented as hydrochloride salt of the L-lysine and were 44.5 g/l and 48.1 g/l, respectively.

Seed Medium (pH 7.0):
20 g of raw sugar, 10 g of peptone, 5 g of yeast extract, 1.5 g of urea, 4 g of $KH_2PO_4$, 8 g of $K_2HPO_4$, 0.5 g of $MgSO_4$ 7 $H_2O$, 100 μg of biotin, 1,000 μg of thiamine HCl, 2,000 μg of calcium pantothenate, 2,000 μg of nicotin amide (1 L of distilled water basis)

Production Medium (pH 7.0):
100 g of raw sugar, 40 g of $(NH_4)_2SO_4$, 2.5 g of soy protein, 5 g of corn steep solids, 3 g of urea, 1 g of $KH_2PO_4$, 0.5 g of $MgSO_4$ 7 $H_2O$, 100 μg of biotin, 1,000 μg of thiamine HCl, 2,000 μg of calcium pantothenate, 3,000 μg of nicotin amide, 30 g of $CaCO_3$ (1 L of distilled water basis)

Example 3

L-lysine Separation From a Culture Medium of *Corynebacterium Glutamicum* KFCC10881-CJP5103

By adding hydrochloride to 1 L of a lysine fermentation broth obtained by culturing *Corynebacterium glutamicum* KFCC10881-CJP5103 in a medium containing molasses and raw sugar, the pH of the fermentation broth was adjusted to pH 2.0, and Ca ions were transformed into $CaSO_4$ and $CaCl_2$. Then, the culture medium was absorbed into a cation exchange resin (Diaion SK-L10), which was reproduced in the form of ammonium, by flowing the culture medium towards the upward direction. After residual bacteria within the cation exchange resin were removed by washing with demineralized water, the high-concentrated lysine was collected by eluting the resin with 2N ammonium hydroxide. The collected solution was concentrated and crystallized by cooling to 20° C., while adjusting the pH to 5.0. A first wet product was obtained by centrifugal separation of a crystallization-completed slurry and a second wet product was obtained by batch concentrating and crystallizing the mother solution. 44 g of a dried lysine product with 98.5% lysine content was obtained by combining the first and second wet products and drying the combined product.

Example 4

L-lysine Separation from a Culture Medium of *Corynebacterium Glutamicum* KFCC10881-CJP5103

By adding sulphuric acid to 1 L of a lysine fermentation broth obtained by culturing *Corynebacterium glutamicum* KFCC10881-CJP5103 in a medium containing molasses and raw sugar, the pH of the fermentation broth was adjusted to pH 2.0. Then, the culture medium was absorbed into a cation exchange resin (Diaion SK-L10), which was reproduced in the form of ammonium, by flowing towards the upward direction. After residual bacteria within the cation exchange resin were removed by washing with demineralized water, the high-concentrated lysine was collected by eluting the resin with 2N ammonium hydroxide. The collected solution was concentrated and crystallized by cooling to 20° C., while adjusting the pH to 5.0 using hydrochloride. A first wet product was obtained by centrifugal separation of a crystallization-completed slurry and a second wet product was obtained by batch concentrating and crystallizing the mother solution. 45 g of a dried lysine product with 99% lysine content was obtained by combining the first and second wet products and drying the combined product.

The microorganism according to the present invention has L-lysine productivity.

In the method of producing L-lysine using the microorganism according to the present invention, L-lysine can be produced at high yield.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A method of producing L-lysine by a fermentation process comprising culturing a microorganism of the genus *Corynebacterium* capable of producing L-lysine, and resistant to kanamycin; and collecting L-lysine from a culture medium, wherein the microorganism is the *Corynebacterium glutamicum* strain KFCC10881 -CJP5103 (Accession No. KCCM-10707P).

* * * * *